US009114205B2

(12) United States Patent
Yokomizo et al.

(10) Patent No.: US 9,114,205 B2
(45) Date of Patent: Aug. 25, 2015

(54) CHEMICAL LIQUID ADDITION SYSTEM AND CHEMICAL LIQUID ADDITION METHOD

(75) Inventors: Tomohisa Yokomizo, Tokyo (JP); Shuichiro Inadome, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 550 days.

(21) Appl. No.: 13/635,074

(22) PCT Filed: Mar. 16, 2011

(86) PCT No.: PCT/JP2011/056169
§ 371 (c)(1),
(2), (4) Date: Sep. 14, 2012

(87) PCT Pub. No.: WO2011/115156
PCT Pub. Date: Sep. 22, 2011

(65) Prior Publication Data
US 2013/0005557 A1    Jan. 3, 2013

(30) Foreign Application Priority Data
Mar. 16, 2010  (JP) .................................. 2010-059384

(51) Int. Cl.
*A61M 1/02*     (2006.01)
*B04B 5/04*     (2006.01)

(52) U.S. Cl.
CPC ........... *A61M 1/0272* (2013.01); *A61M 1/0218* (2014.02); *B04B 5/0428* (2013.01)

(58) Field of Classification Search
CPC .............. B04B 5/0428; A61M 1/0209; A61M 1/0218; A61M 1/0259; A61M 1/0263; A61M 1/0268; A61M 1/0272; A61M 1/0281; A61M 1/029

USPC .................. 494/45; 604/6.07, 408–410, 416; 210/781, 782, 787

See application file for complete search history.

(56) References Cited

U.S. PATENT DOCUMENTS 4,223,675 A    9/1980   Williams
5,456,824 A    10/1995  Misumi et al.
(Continued)

FOREIGN PATENT DOCUMENTS

EP    0600804     12/1993
JP    6-218039    8/1994
(Continued)

OTHER PUBLICATIONS

European search report issued with respect to application No. 11756340.3, mail date is Dec. 11, 2014.
(Continued)

*Primary Examiner* — Timothy Cleveland
(74) *Attorney, Agent, or Firm* — Greenblum & Bernstein, P.L.C.

(57) ABSTRACT

The preservation liquid addition system of the present invention enables a chemical liquid to be added to a blood cell component both easily and in a short period of time. The preservation liquid addition system is able to be placed on a centrifugal separator. The preservation liquid addition system has a blood bag, a preservation liquid bag, a mixed liquid bag, a first flow path and a static mixer. A blood component in the blood bag and a preservation liquid in the preservation liquid bag are sent to the static mixer through the first flow path, and a mixed liquid mixed by the static mixer is sent to the mixed liquid bag by centrifugal force of the centrifugal separator.

13 Claims, 7 Drawing Sheets

(56) References Cited

U.S. PATENT DOCUMENTS

| | | | |
|---|---|---|---|
| 2003/0138349 A1* | 7/2003 | Robinson et al. | 604/4.01 |
| 2007/0282242 A1 | 12/2007 | Gibbs et al. | |
| 2007/0284320 A1 | 12/2007 | Menhennett et al. | |
| 2008/0135462 A1 | 6/2008 | Park et al. | |

FOREIGN PATENT DOCUMENTS

| | | |
|---|---|---|
| JP | 7-80058 | 3/1995 |
| JP | H07-80058 A | 3/1995 |
| JP | 2008-145420 | 6/2008 |
| JP | 2008-145420 A | 6/2008 |

OTHER PUBLICATIONS

Search report from International Application No. PCT/JP2011/056169, mail date is Jun. 21, 2011.

International Preliminary Report on Patentability issued with respect to International Application No. PCT/JP2011/056169, mail date is Oct. 23, 2012.

* cited by examiner

CHEMICAL LIQUID ADDITION SYSTEM AND CHEMICAL LIQUID ADDITION METHOD

BACKGROUND

The present invention relates to a chemical liquid addition system and a chemical liquid addition method.

In order to perform a component transfusion, for example, it is necessary to prepare a blood component preparation by separating blood components such as packed red blood cell components or plasma components from blood. Blood cell preparations are prepared by, for example, separating blood collected in a blood bag into multiple blood components by centrifugal separation, and removing pathogenic substances such as white blood cells from the blood components with a filter.

In addition, it is also necessary to add a preservation liquid to blood component preparations in order to store blood components for long periods of time and maintain quality. This preservation liquid is added during preparation of the above-mentioned blood component preparation. However, since red cell components separated by centrifugal separation, for example, demonstrate extremely high Ht values and have difficulty in passing through a filter, preservation liquid is added prior to passing the red cell component through the filter for the additional purpose of diluting the red cell component. If a red cell component having a high Ht value were to be passed through a filter, there is the risk of the red blood cells being destroyed and clogging the filter.

In addition, since red cell components having a high Ht value are also viscous and do not easily mix with the preservation liquid simply by being added thereto, if these red cell components are passed through a filter as is, there is again the risk of the red cell components being destroyed and clogging the filter. Accordingly, it is necessary that red cell components and preservation liquid be adequately mixed.

The above-mentioned cell component preparations are prepared using a system in which a plurality of blood bags are connected with tubes since they are required to be prepared aseptically. For example, as shown in FIG. 7, this type of system 100 has a blood bag 101, a preservation liquid bag 102, a mixing bag 103, a blood component bag 104 and tubes 105 that connect them.

When preparing a blood component preparation, the system 100 is placed on a centrifugal separator, and blood in the blood pack is centrifugally separated into multiple blood component layers by the centrifugal separator. Next, the system 100 is removed from the centrifugal separator, placed on a blood component separation device having an extruding function, for example (see Patent Document 1) where the plasma component of the blood component layers is extruded from the blood bag and separated, and then transferred to the blood component bag 104 as a plasma preparation. In addition, the blood component layer having red blood cells is transferred to the mixing bag 103 in the blood component separation device. At this time, a preservation liquid is supplied from the preservation liquid bag 102 to the mixing bag 103. Next, the system 100 is removed from the blood component separation device, and the mixing bag 103 is shaken manually, for example, to agitate and mix the red cell component containing red blood cells with the preservation liquid. Subsequently, the mixing bag 103 is suspended above and the red cell component and preservation liquid in the mixing bag 103 are passed through a filter using the difference in gravity and the like to remove white blood cells and prepare packed red blood cell components.

[Patent Document 1] Patent Publication JP-A-H6-218039

However, addition of the preservation liquid using the system 100 in the manner described above is carried out by centrifugally separating blood with a centrifugal separator followed by transferring the system 100 to a blood component separation device where the red cell component is transferred to the mixing bag 103, the system 100 is subsequently removed from the blood component separation device and the mixing bag is shaken well to mix the red cell component and the preservation liquid. Consequently, addition of the preservation liquid is both bothersome and time-consuming. In addition, two devices consisting of the centrifugal separator and the blood component separation device are required, thereby resulting in increased costs.

SUMMARY

With the foregoing in view, an object of the present invention is to provide a chemical liquid addition system enabling a chemical liquid such as a preservation liquid to be added to a body fluid component such as a blood component both easily and in a short period of time while also reducing costs by reducing the number of devices used, and a chemical liquid addition method that uses this chemical liquid addition system.

In order to achieve the above-mentioned object, the present invention provides a chemical liquid addition system that is placed on a centrifugal separator and that adds a chemical liquid to a body fluid component of a body fluid, and has: a body fluid bag that holds a body fluid; a chemical liquid bag that holds a chemical liquid; a mixed liquid bag that holds a mixed liquid of the body fluid component of the body fluid and the chemical liquid; a flow path that connects the body fluid bag, the chemical liquid bag and the mixed liquid bag; and a mixing device that mixes the body fluid component sent from the body fluid bag with the chemical liquid sent from the chemical liquid bag in the flow path while the body fluid component and the chemical liquid flow therethrough, wherein the body fluid component of body fluid in the body fluid bag and the chemical liquid in the chemical liquid bag are sent to the mixing device through the flow path, and the mixed liquid mixed by the mixing device is sent to the mixed liquid bag, by centrifugal force of the centrifugal separator.

According to the present invention, since a chemical liquid can be added to a body fluid component present in body fluid together with centrifugally separating the body fluid using the centrifugal force of a centrifugal separator, the chemical liquid can be added both easily and in a short period of time. In addition, since processing from centrifugal separation of body fluid to addition of chemical liquid can be carried out with a centrifugal separator alone, costs can be reduced.

The above-mentioned flow path may be connected to ends of the body fluid bag and the chemical liquid bag in a direction of centrifugal force of the centrifugal separator when the system is placed on the centrifugal separator. In this case, the body fluid component and the chemical liquid can be efficiently transferred to the mixing device by using the centrifugal force of the centrifugal separator.

The chemical liquid addition system may also have a body fluid component bag holding a body fluid component other than the body fluid component that flows to the flow path; and another flow path that connects the body fluid bag and the body fluid component bag. In addition, this another flow path may also be connected to the end of the body fluid bag on the side in the direction of centrifugal force of the centrifugal separator when the system is placed on the centrifugal separator. In this case, the other body fluid component can be efficiently sent to the body fluid component bag by using the centrifugal force of the centrifugal separator.

In the chemical liquid addition system as described above, the body fluid may be blood, the body fluid component flowing to the flow path may be a red cell component composed mainly of red blood cells, and the chemical liquid may be a preservation liquid for preserving the red cell component.

A filter that removes a predetermined undesired substance from the mixed liquid may be provided in the flow path. In this case, since the undesired substance can be removed from the mixed liquid by sending the mixed liquid to a filter using the centrifugal force of the centrifugal separator, processing from centrifugal separation of body fluid to removal of undesired substances can be carried out both easily and in a short period of time.

According to another aspect thereof, the present invention provides a method for adding a chemical liquid to a body fluid component of body fluid in use of the above-mentioned chemical liquid addition system, this method comprising: a step in which body fluid in the body fluid bag is separated into a plurality of body fluid components by the centrifugal force of a centrifugal separator; and a step in which, by the centrifugal force of the centrifugal separator, at least one body fluid component in the body fluid bag and a chemical liquid in the chemical liquid bag are sent to the mixing device through the flow path and mixed therein; the mixed liquid of the body fluid component and the chemical liquid is sent to the mixed liquid bag and held therein.

According to the present invention, since a chemical liquid can be added to a body fluid component present in body fluid together with centrifugally separating the body fluid using the centrifugal force of a centrifugal separator, the chemical liquid can be added both easily and in a short period of time. In addition, since processing from centrifugal separation of body fluid to addition of chemical liquid can be carried out with a centrifugal separator alone, costs can be reduced.

In addition, according to another aspect thereof, the present invention provides a method for adding a chemical liquid to a body fluid component of body fluid using the above-mentioned chemical liquid addition system having a filter, this method comprising: a first step in which body fluid in the body fluid bag is separated into a plurality of body fluid components by the centrifugal force of a centrifugal separator; and a second step in which, by the centrifugal force of the centrifugal separator, at least one body fluid component in the body fluid bag and a chemical liquid in the chemical liquid bag are sent to the mixing device through the flow path and mixed therein; a predetermined undesired substance is removed from the mixed liquid of the body fluid component and the chemical liquid through a filter; and the resultant mixed liquid of the body fluid component and the chemical liquid is sent to the mixed liquid bag and held therein.

According to the present invention, since centrifugal separation of body fluid and addition of a chemical liquid to a body fluid component in the body fluid can be carried out using the centrifugal force of a centrifugal separator, the chemical liquid can be added both easily and in a short period of time. In addition, since processing from centrifugal separation of body fluid to addition of chemical liquid can be carried out with a centrifugal separator alone, costs can be reduced. Moreover, since removal of undesired substances from the mixed liquid can also be carried out using the centrifugal force of a centrifugal separator, processing from centrifugal separation of body fluid to removal of undesired substances can be carried out easily and in a short period of time.

In the above-mentioned first step, a plurality of separation layers having different concentrations of the predetermined undesired substance may be formed from the body fluid, and in the above-mentioned second step, the plurality of separation layers may be sent to the filter in order starting with the layer having the highest concentration. In this case, the separation layer having the highest concentration of the predetermined undesired substance can be initially passed through the filter while the filtration capacity of the filter is high, and separation layers having lower concentrations of the undesired substance can be passed through the filter as the filtration capacity of the filter decreases due to clogging and the like. As a result, since the undesired substance can be adequately removed over the entire filtration process carried out on the plurality of separation layers, the removal rate of undesired substances of the filter can be enhanced. In addition, since the size of the filter can be reduced corresponding to the increase in filter removal rate, in this case, the amount of useful substances recovered by the filter can be decreased.

In still another aspect thereof, the present invention provides a method for adding a chemical liquid to a body fluid component of body fluid in use of a body fluid bag holding body fluid, a chemical liquid bag holding a chemical liquid, a mixed liquid bag holding a mixed liquid of the body fluid component of the body fluid and the chemical liquid, a flow path that connects the body fluid bag, the chemical liquid bag and the mixed liquid bag, a mixing device that mixes in the flow path the body fluid component sent from the body fluid bag with the chemical liquid sent from the chemical liquid bag while the body fluid component and the chemical liquid flow therethrough; and a centrifugal separator that centrifugally separates the body liquid in the body liquid bag, this method comprising: a step of implementing centrifugal separation of body fluid in the body fluid bag and separating the same into a plurality of body fluid components by the centrifugal separator, a step of sending the separated body fluid components in the body fluid bag and the chemical liquid in the chemical liquid bag to the mixing device through the flow path by centrifugal force of the centrifugal separator, a step of mixing the body fluid components with the chemical liquid by the mixing device, and a step of sending the mixed liquid that has been mixed to the mixed liquid bag through the flow path.

According to the present invention, a chemical liquid can be added to a body fluid component both easily and in a short period of time. In addition, the number of devices used can be reduced, thereby making it possible to reduce costs.

DETAILED DESCRIPTION

Figure 1:
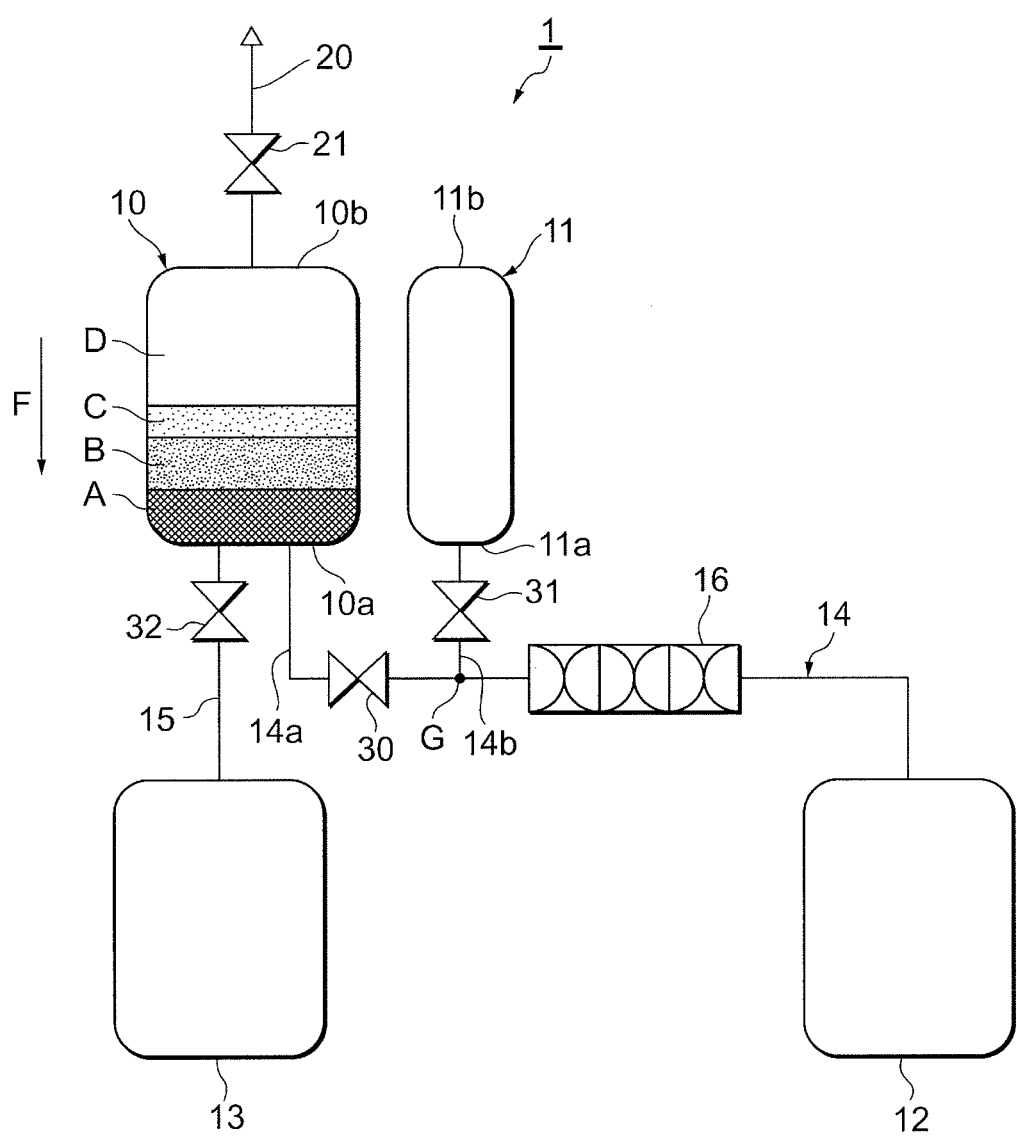
FIG. 1 is an explanatory diagram showing an overview of the configuration of a preservation liquid addition system.

The following provides an explanation of preferred embodiments of the present invention with reference to the drawings. FIG. 1 is an explanatory drawing showing an overview of the configuration of a preservation liquid addition system 1 as an example of a chemical liquid addition system according to the present embodiment.

The preservation liquid addition system 1 has, for example, a blood bag 10 as a body fluid bag, a preservation liquid bag 11 as a chemical liquid bag, a mixed liquid bag 12, a blood component bag 13 as a body fluid component bag, a first flow path 14, a second flow path 15 as a another flow path, and a static mixer 16 as a mixing device, which can be placed on a centrifugal separator 2 (to be described later).

The blood bag 10 and the preservation liquid bag 11 are formed with, for example, a soft resin and are able to freely deform. A blood collection flow path 20 is connected to the blood bag 10 and the blood bag 10 is able to hold blood collected from a human body together with an anticoagulant. A switching valve 21 that opens and closes the blood collection flow path 20 is provided in the flow path 20. A preservation liquid for preserving, for example, a red cell component consisting mainly of red blood cells, is held in the preservation liquid bag 11.

The mixed liquid bag 12 and the blood component bag 13 are formed from, for example, a soft resin and are able to freely deform.

A soft tube, for example, is used for the first flow path 14 and the second flow path 15. One end of the first flow path 14 is divided into two branches consisting of branches 14a and 14b, and the branches 14a and 14b are connected to the blood bag 10 and the preservation liquid bag 11. The branches 14a and 14b merge at an intermediate point, and the other end of the first flow path 14 is connected to the mixed liquid bag 12. The branch 14a is connected to a first end 10a of the blood bag 10 on the side in the direction of centrifugal force F of the centrifugal separator 2 when, for example, the blood bag 10 has been placed on the centrifugal separator 2. The branch 14b is connected to a first end 11a of the preservation liquid bag 11 on the side in the direction of centrifugal force F of the centrifugal separator 2 when, for example, the preservation liquid bag 11 has been placed on the centrifugal separator 2.

The second flow path 15 is connected to the first end 10a of the blood bag 10. Furthermore, the above-mentioned blood collection flow path 20 is connected to a second end 10b on the opposite side of the direction of centrifugal force F.

Switching valves 30 and 31 that open and close their respective flow paths are respectively provided in the branches 14a and 14b of the first flow path 14. In addition, a switching valve 32 that opens and closes the second flow path 15 is provided in the second flow path 15.

The static mixer 16 is able to agitate and mix a red cell component sent from the blood bag 10 and preservation liquid sent from the preservation liquid bag 11 in the first flow path 14 while allowing to flow there through, and allows the mixed liquid to flow to the side of the mixed liquid bag 12.

Figure 2:
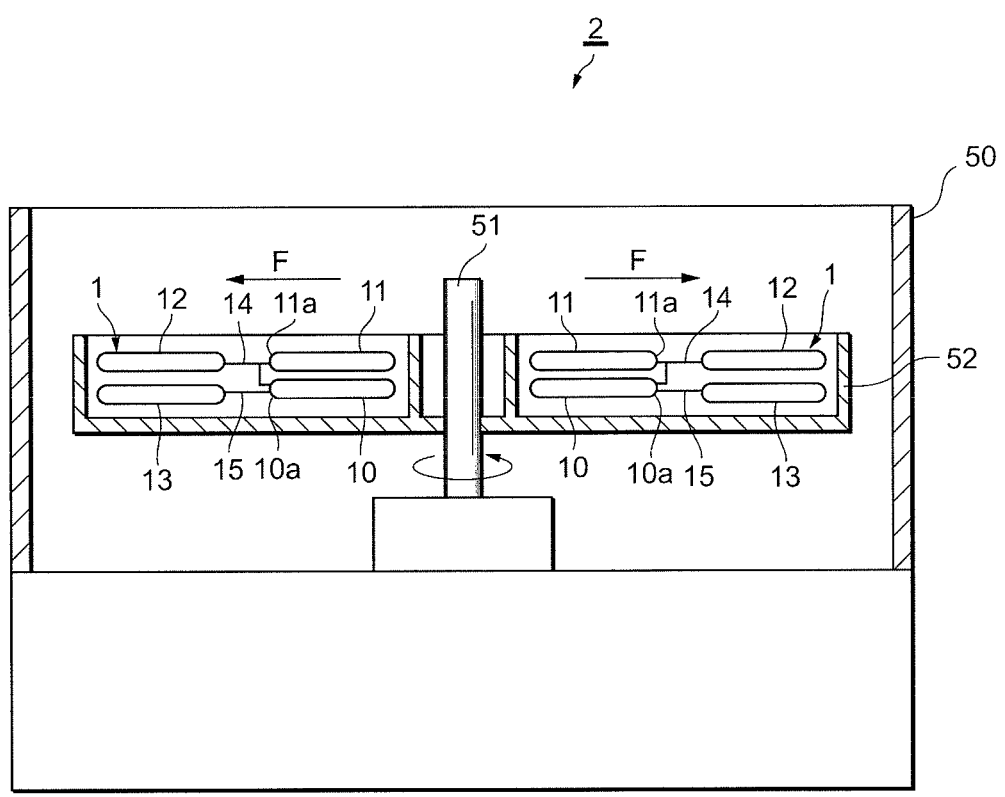
FIG. 2 is a longitudinal cross-sectional view showing an overview of the configuration of a centrifugal separator.
Figure 3:
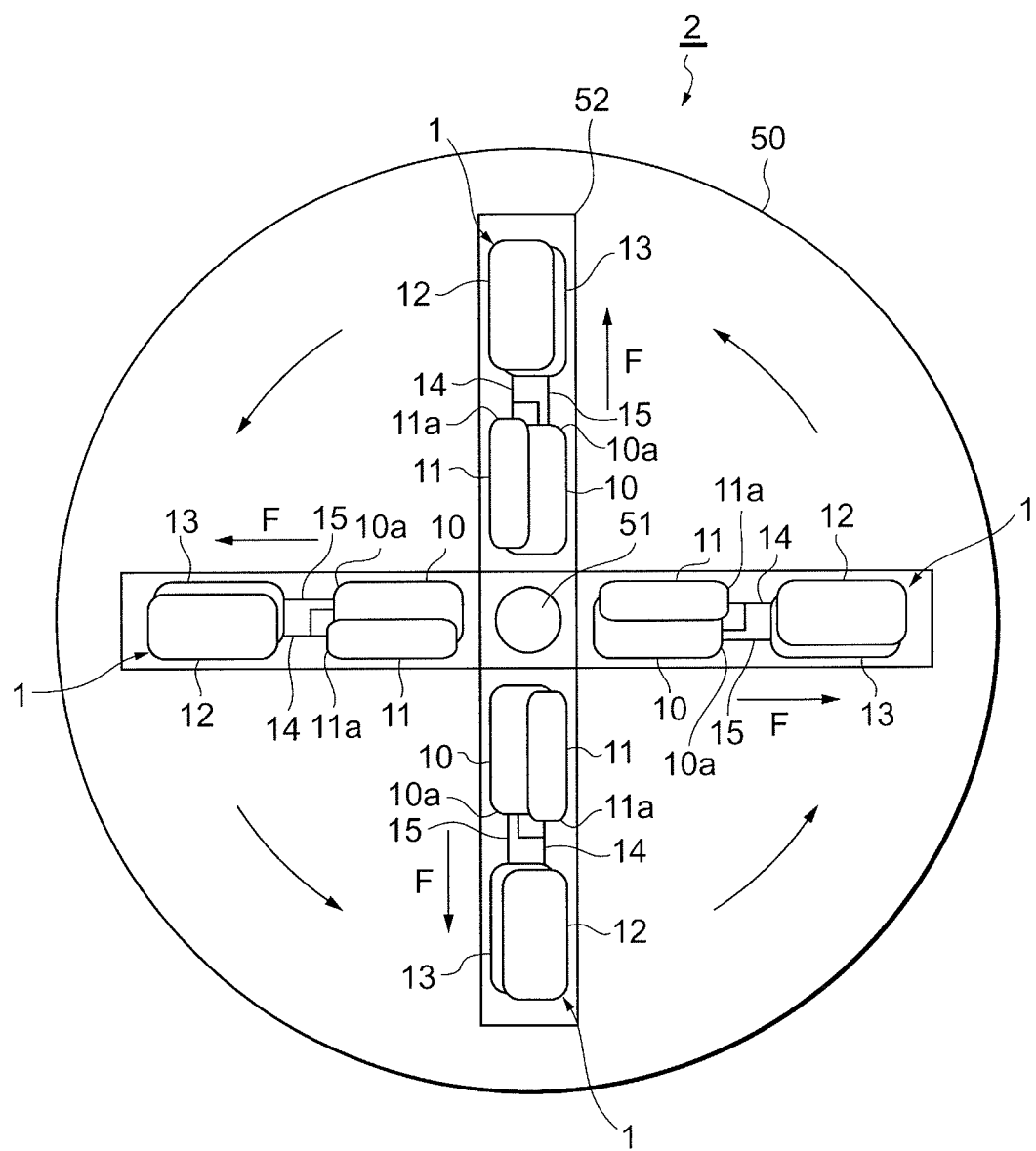
FIG. 3 is an overhead view showing an overview of the configuration of a centrifugal separator.

As shown in FIGS. 2 and 3, for example, the centrifugal separator 2 has a rotation driving unit 51 such as a motor, and a rotating container 52 that is rotated by the rotation driving unit 51 and is capable of housing a plurality of the preservation liquid addition systems 1, in a case 50. The blood bag 10 and the preservation liquid 11 of the preservation liquids addition system 1, for example, can be installed in the rotating container 52 such that the first end 10a, to which is connected the branch 14a of the first flow path 14 and the second flow path 15, and the first end 11a, to which is connected the branch 14b, are facing towards the outside (side in the direction of the centrifugal force F).

Next, an explanation is provided of a preservation liquid addition method that uses the preservation liquid addition system 1 composed in the manner described above.

First, body fluid in the form of blood collected from a human body is introduced into the blood bag 10 through the blood collection flow path 20 shown in FIG. 1 and held therein. At this time, the switching valves 30, 31 and 32 are closed. An anticoagulant is added to the blood in the blood bag 10. Next, as shown in FIGS. 2 and 3, the preservation liquid addition system 1 is placed in the rotating container 52 of the centrifugal separator 2. At this time, the blood bag 10 is installed so that the side of the first end 10a is facing in the direction of the centrifugal force F, and the preservation liquid bag 11 is installed so that the end of the first end 11a is facing in the direction of the centrifugal force F.

Next, the centrifugal separator 2 is operated, the rotating container 52 is rotated by the rotation driving unit 51, and blood in the blood bag 10 is separated into, for example, four separation layers A, B, C and D in the direction of centrifugal force F as shown in FIG. 1 by the resulting centrifugal force. For example, the separation layers A to C may be red cell component layers containing red blood cells, while the separation layer D may be a plasma separation layer containing plasma. In addition, the separation layers A to D have different concentrations (concentrations in percent by weight) of undesired substances in the form of white blood cells. The concentrations of white blood cells may be in the order, for example, C, B and A with C being the highest concentration (A<B<C), and the concentration of white blood cells in separation D is lower than that of separation layer C. Furthermore, the concentration of red blood cells is in the order of A, B and C with the highest concentration in separation layer A (A>B>C), and separation layer C contains the largest number of platelets.

Next, as a result of opening the switching valves 30 and 31 and subsequently operating the centrifugal separator 2, the separation layers A, B and C flow into the branch 14a of the first flow path 14 in order starting with the separation layer closest to the first end 10a due to centrifugal force. In addition, simultaneous thereto, preservation liquid flows into the branch 14b of the first flow path 14 from the preservation liquid bag 11 due to centrifugal force. The red cell component of each separation layer A to C merges with the preservation liquid at a junction G in the first flow path 14 and then flows to the static mixer 16. The red cell components and the preservation liquid are agitated and mixed while flowing through the static mixer 16. As a result, the red cell component of each of the separation layers A to C is uniformly mixed with the preservation liquid to form a mixed liquid.

The mixed liquid that has passed through the static mixer 16 flows into the mixed liquid bag 12 and is held therein.

After all of the separation layers A to C have been discharged from the blood bag 10, the switching valves 30 and 31 are then closed and the switching valve 32 is opened. At this time, the centrifugal separator 2 is again operated and the separation layer D in the blood bag 10 is sent to the blood component bag 13 through the second flow path 15 and held therein due to the centrifugal force thereof. As a result, a plasma component consisting mainly of plasma is held in the blood component bag 13. Subsequently, the switching valve 32 is closed, thereby completing the series of preservation liquid addition processing. Subsequently, the mixed liquid in the mixed liquid bag 12 is passed through a filter to remove white blood cells from the red cell component to prepare packed red blood cell components.

According to the present invention described above, since blood components can be separated and a preservation liquid can be added to a red cell component using the centrifugal force of the centrifugal separator 2, the preservation liquid can be added both easily and in a short period of time. In addition, since processing from centrifugal separation of blood to addition of preservation liquid can be carried out with the centrifugal separator 2 alone, costs can be reduced. Furthermore, although separation of blood components in the blood bag 10 and supply of blood components and preservation liquid from the blood bag 10 and the preservation liquid bag 11 to the mixed liquid bag 12 are carried out continuously in the above-mentioned embodiment, they may also be carried out at intervals.

Since the branch 14a of the first flow path 14 is connected to the first end 10a of the blood bag 10 on the side in the direction of centrifugal force F, and the branch 14b is connected to the first end 11a of the preservation liquid bag 11 on the side in the direction of centrifugal force F, red cell components and preservation liquid can be efficiently sent to the static mixer 16 using the centrifugal force of the centrifugal separator 2.

Since the preservation liquid addition system 1 has the blood component bag 13 that holds blood components and the second flow path 15 connecting the blood component bag 13 and the blood bag 10, a plasma component preparation can be prepared by separating and housing a plasma component in the preservation liquid addition system 1.

In addition, since the second flow path 15 is connected to the first end 10a of the blood bag 10 on the side in the direction of centrifugal force F, a plasma component can be efficiently sent to the blood component bag 13 using centrifugal force of the centrifugal separator 2.

Figure 4:
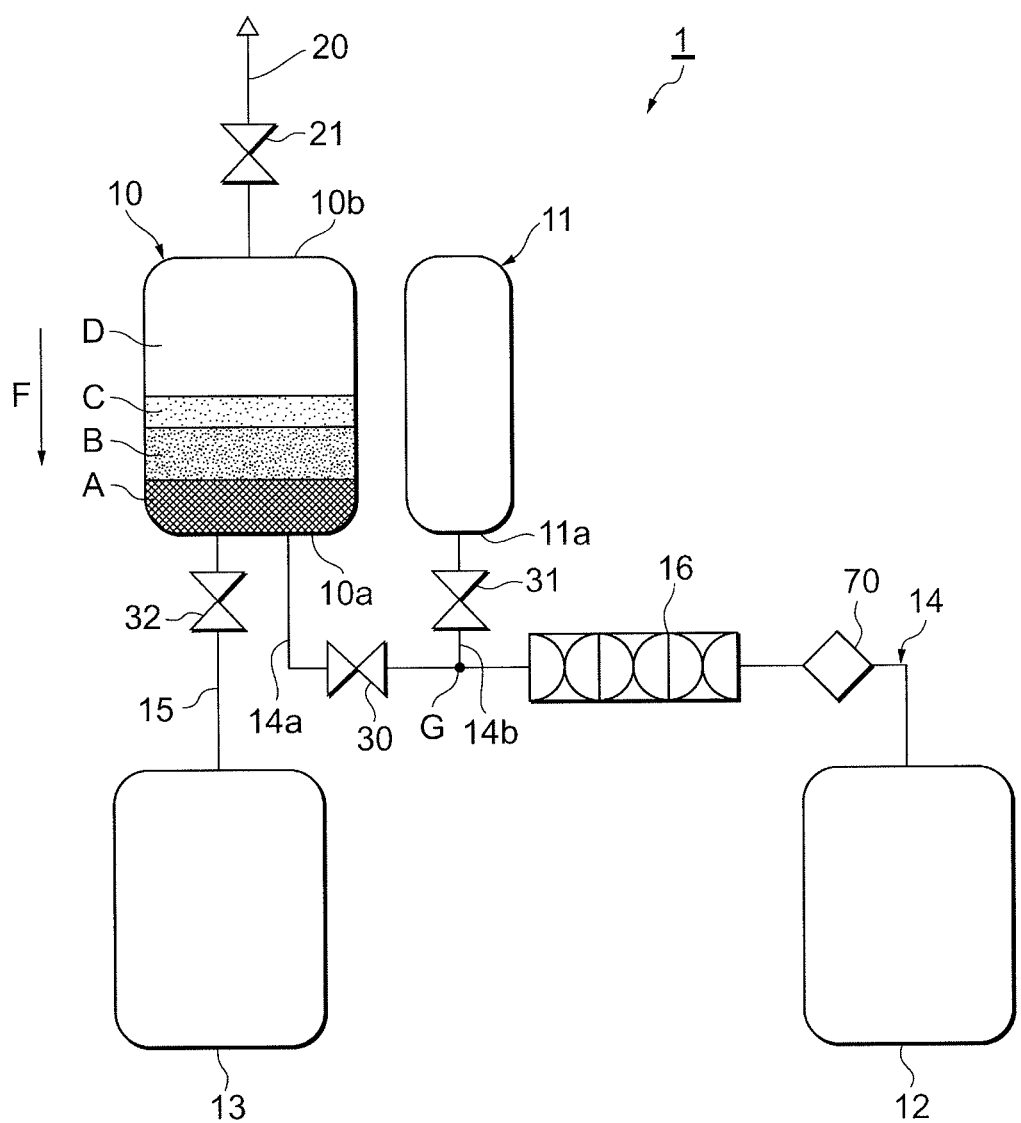
FIG. 4 is an explanatory drawing showing an overview of the configuration of a preservation liquid addition system having a filter.

A filter 70 that removes white blood cells from the red cell component in the mixed liquid may be provided in the first flow path 14 as shown in FIG. 4 in the preservation liquid addition system 1 of the above-mentioned embodiment. The filter 70 is formed from a porous body, for example, capable of filtering white blood cells. The filter 70 is provided between the static mixer 16 and the mixed liquid bag 12.

In this case, the red cell components of the separation layers A to C separated in the blood bag 10 and the preservation liquid in the preservation liquid bag 11 are sent to the static mixer 16 through the first flow path 14 and mixed therein due to centrifugal force of the centrifugal separator 2, after which the mixed liquid is passed through the filter 70 to remove white blood cells from the red cell components. Subsequently, the mixed liquid is sent to the mixed liquid bag 12 and held therein to prepare packed red blood cell components.

According to this example, since white blood cells can be removed from red cell components using the centrifugal force of the centrifugal separator 2, processing from separation of blood components to preparation of packed red blood cell components, for example, can be carried out easily and in a short period of time.

In addition, in this example, a plurality of separation layers A to C having different concentrations of white blood cells are formed, and the plurality of separation layers A to C are sent to the filter 70 in order starting with the separation layer having the highest white blood cell concentration (in the order of A, B and then C). Consequently, the separation layer A having the highest white blood cell concentration can be initially passed through the filter 70 while the filtration capacity of the filter 70 is high, and the separation layers B and C having lower concentrations of white blood cells can be passed through the filter 70 as the filtration capacity of the filter 70 decreases due to clogging and the like. As a result, since white blood cells can be adequately removed over the entire filtration process carried out on the separation layers A to C, the removal rate of white blood cells of the filter 70 can be enhanced. Furthermore, since blood separation status is influenced by such factors as the manner in which centrifugal force is applied or the duration thereof, blood may not necessarily be separated as in the present embodiment, and the present invention is naturally not limited to the separation state exemplified herein.

Although the above-mentioned description has provided an explanation of a preferred embodiment of the present invention with reference to the drawings, the present invention is not limited thereto. A person with ordinary skill in the art is clearly able to conceive of various alterations or modifications within the scope of the technical idea described in the claims, and it should be understood that these alterations or modifications are naturally included in the technical scope of the present invention.

Figure 5:
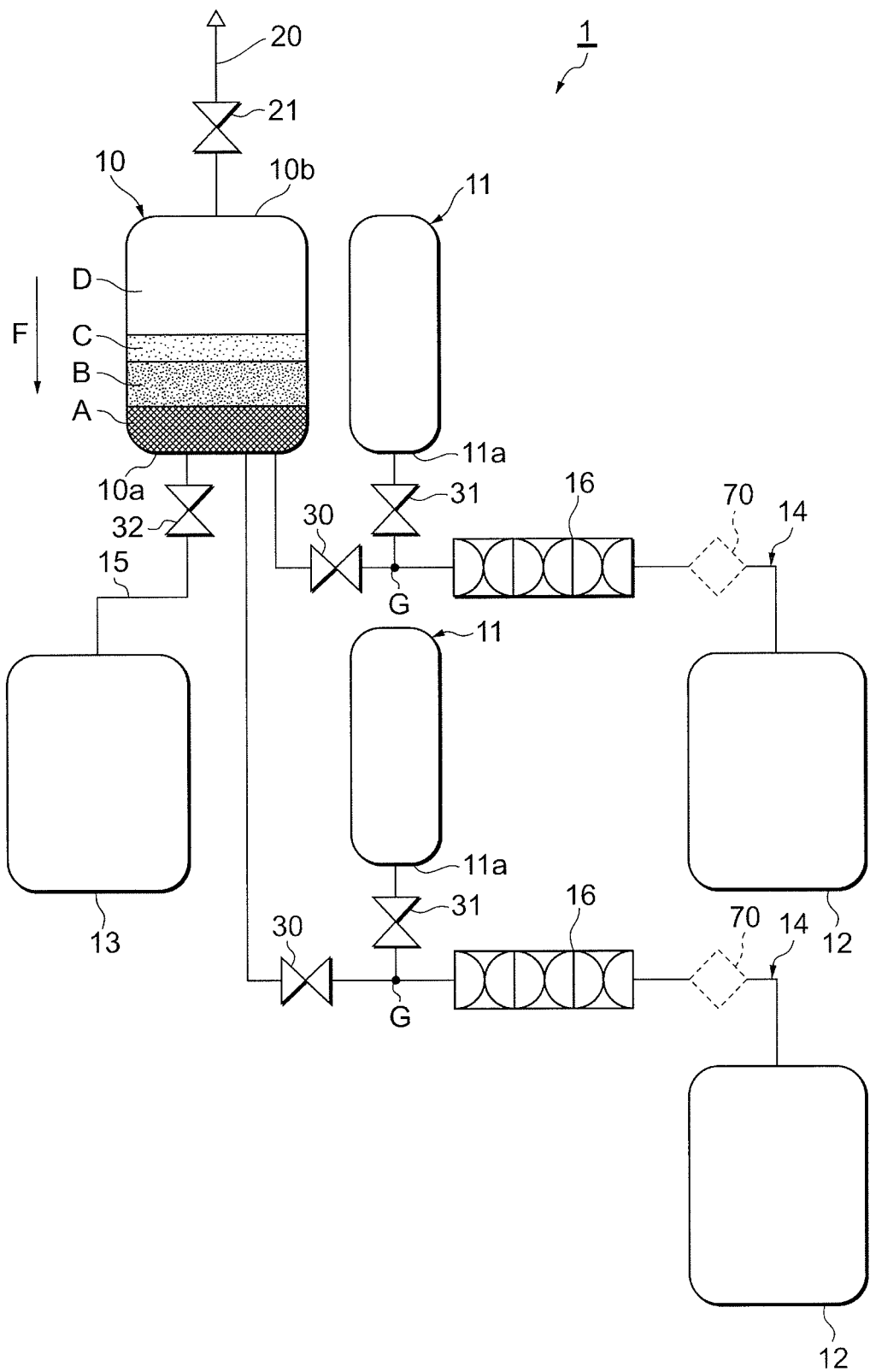
FIG. 5 is an explanatory drawing showing an overview of the configuration of a preservation liquid addition system having multiple channels.

For example, although the preservation liquid was added to only one type of blood component in the preservation liquid addition system 1 of the above-mentioned embodiment, preservation liquid may be added to two or more types of blood components. In this case, as shown in FIG. 5, a plurality of channels at least having the preservation liquid bag 11, the mixed liquid bag 12, the first flow path 14 and the static mixer 16 may be provided in the preservation liquid addition system 1. The example shown in FIG. 5 indicates the case of having two channels. As a result, respective preservation liquids can be added to a plurality of blood components separated in the blood bag 10 to form their respective mixed liquids. Furthermore, the above-mentioned filter 70 may be included in each of the plurality of channels. In addition, a plurality of blood component bags 13 may also be provided for blood components to which preservation liquid is not added.

Figure 6:
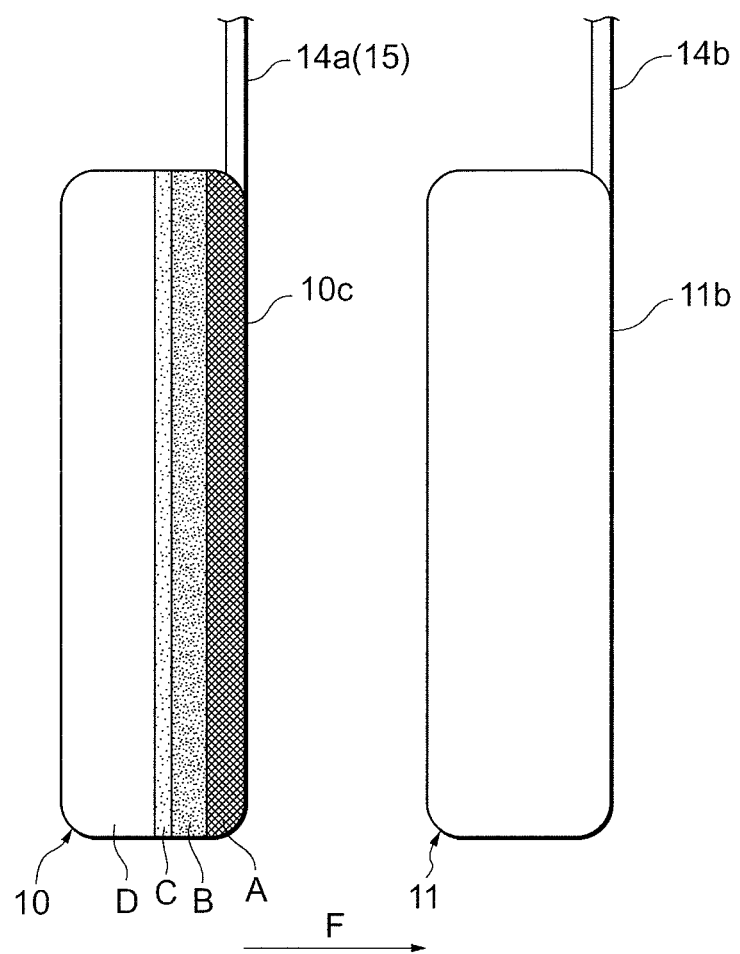
FIG. 6 is an explanatory drawing showing a connection example of a flow path in the case a blood bag and a preservation liquid bag are installed longitudinally in a centrifugal separator.
Figure 7:
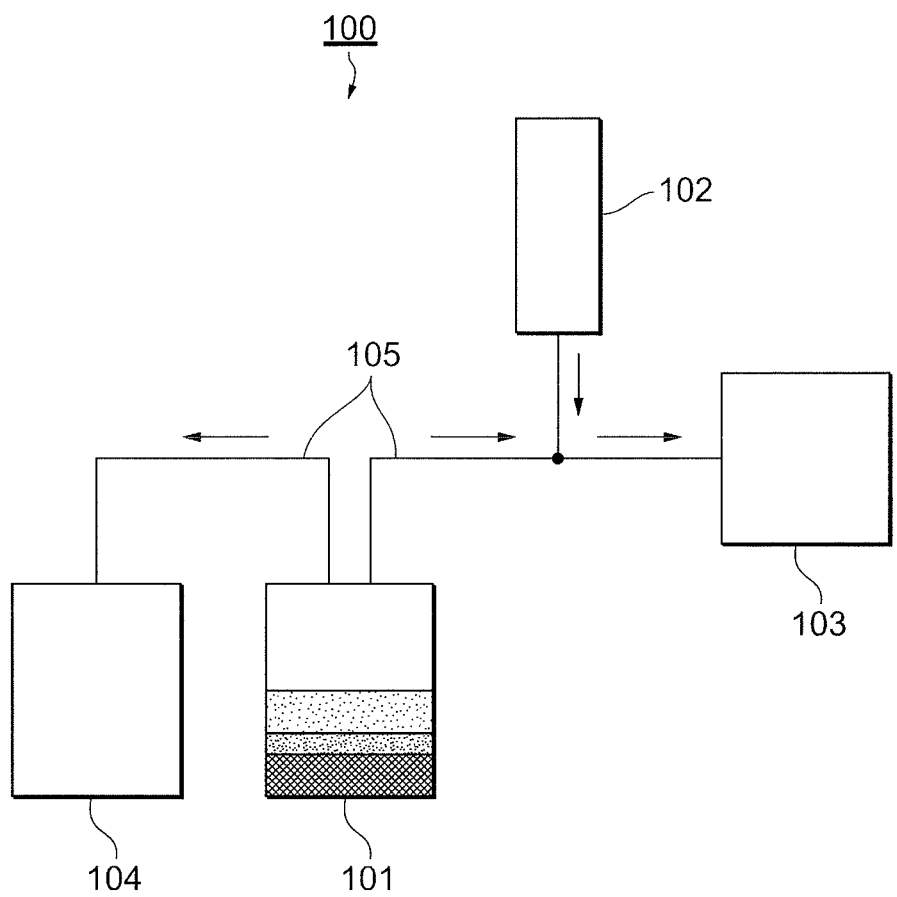
FIG. 7 is a schematic diagram showing a system prior to modification.

Although the above-mentioned embodiment described an example of the case of the blood bag 10 and the preservation liquid bag 11 being installed so that the lengthwise direction of the bags (vertical direction in FIG. 1) is facing in the direction of centrifugal force F when the preservation liquid addition system 1 is placed on the centrifugal separator 2, as shown in FIG. 6, in the case the blood bag 10 and the preservation liquid bag 11 are installed so that the direction of thickness of the bags (lateral direction in FIG. 6) is in the direction of centrifugal force F, the branch 14a of the first flow path 14 and the second flow path 15, as well as the branch 14b, may be made to be respectively connected to ends 10c and 11b on the outside of the blood bag 10 and the preservation liquid bag 11 in the direction of thickness thereof. Furthermore, if the mixed liquid bag 12 and the blood component bag 13 are arranged at locations where centrifugal force acts more strongly than on the blood bag 10 and the preservation liquid bag 11, the branches 14a and 14b of the first flow path 14 and the second flow path 15 shown in FIG. 1 may be respectively connected to the sides of the ends 10b and 11b of the blood bag 10 and the preservation liquid bag 11 on the opposite side from the direction of centrifugal force F. In this case, the contents of the blood bag 10 and the preservation liquid bag 11 can be sent to the mixed liquid bag 12 and the blood component bag 13 by centrifugal force by utilizing the principle of a siphon.

Although the static mixer 16 was used as a mixing device in the above-mentioned embodiment, another type of mixing device may be used provided it has a mixing function. In addition, although the undesired substance removed by the filter 70 consisted of white blood cells in the above-mentioned embodiment, other undesired substances such as platelets or red blood cells may also be removed corresponding to the preparation to be ultimately prepared. In addition, although blood was used as body fluid in the above-mentioned embodiment, the present invention can also be applied in the case of using other body fluids such as bone marrow or umbilical cord blood. In addition, the chemical liquid is not limited to a preservation liquid such as mannitol adenine phosphate (MAP) liquid, saline adenine glucose mannitol (SAGM) liquid or additive liquid 1 (AS-1), but rather an anticoagulant such as citrate-phosphate-dextrose with adenine (CPD-A) may also be added. In addition, dimethylsulfoxide (DMSO), which is used for frozen storage of cells obtained from bone marrow umbilical cord blood, may also be used for the preservation liquid. In addition, a buffer such as phosphate buffered saline (PBS), which is used to replace DMSO present with cells obtained from bone marrow or umbilical cord blood following frozen storage, may also be used for the preservation liquid.

The present invention is useful when carrying out addition of a chemical liquid to a body fluid component both easily and in a short period of time.

1 Preservation liquid addition system
2 Centrifugal separator
10 Blood bag
10a First end
11 Preservation liquid bag
11a First end
12 Mixed liquid bag
13 Blood component bag
14 First flow path
15 Second flow path
16 Static mixer
A to D Separation layers
F Direction of centrifugal force

We claim:

1. A chemical liquid addition system that is placed on a centrifugal separator and that adds a chemical liquid to a body fluid component of a body fluid, comprising:
the body fluid bag that holds a body fluid;
a chemical liquid bag that holds a chemical liquid;
a mixed liquid bag that holds a mixed liquid of the body fluid component of the body fluid and the chemical liquid;
a flow path that connects the body fluid bag, the chemical liquid bag and the mixed liquid bag; and
a mixing device that mixes the body fluid component sent from the body fluid bag with the chemical liquid sent from the chemical liquid bag in the flow path while the body fluid component and the chemical liquid flow therethrough, wherein,
the body fluid component of body fluid in the body fluid bag and the chemical liquid in the chemical liquid bag are sent to the mixing device through the flow path, and the mixed liquid mixed by the mixing device is sent to the mixed liquid bag, by centrifugal force of the centrifugal separator.

2. The chemical liquid addition system according to claim 1, wherein the flow path is connected to ends of the body fluid bag and the chemical liquid bag in a direction of centrifugal force of the centrifugal separator when the system is placed on the centrifugal separator.

3. The chemical liquid addition system according to claim 1, comprising:
a body fluid component bag holding a body fluid component other than the body fluid component that flows to the flow path; and
another flow path that connects the body fluid bag and the body fluid component bag.

4. The chemical liquid addition system according to claim 3, wherein the another flow path is connected to the end of the body fluid bag on the side in a direction of centrifugal force of the centrifugal separator when the system is placed on the centrifugal separator.

5. The chemical liquid addition system according to claim 1, wherein
the body fluid is blood,
the body fluid component flowing to the flow path is a red cell component composed mainly of red blood cells, and
the chemical liquid is a preservation liquid for preserving the red cell component.

6. The chemical liquid addition system according to claim 1, wherein a filter that removes a predetermined undesired substance from the mixed liquid is provided in the flow path.

7. A chemical liquid addition method for adding a chemical liquid to a body fluid component of a body fluid in use of:
a body fluid bag holding the body fluid;
a chemical liquid bag holding a chemical liquid;
a mixed liquid bag;
a flow path that connects the body fluid bag, the chemical liquid bag and the mixed liquid bag;
a mixing device that mixes in the flow path the body fluid component sent from the body fluid bag with the chemical liquid sent from the chemical liquid bag while the body fluid component and the chemical liquid flow therethrough; and
a centrifugal separator that centrifugally separates the body fluid in the body fluid bag, the method comprising:
a step of separating the body fluid in the body fluid bag into a plurality of body fluid components by the centrifugal separator,
a step of sending at least one of the separated body fluid components in the body fluid bag and the chemical liquid in the chemical liquid bag to the mixing device through the flow path by centrifugal force of the centrifugal separator,
a step of mixing the at least one of the separated body fluid components with the chemical liquid by the mixing device, and
a step of sending the mixed liquid that has been mixed to the mixed liquid bag through the flow path.

8. The chemical liquid addition method according to claim 7, comprising:
a step of removing a predetermined undesired substance from the mixed liquid through a filter.

9. The chemical liquid addition method according to claim 8, wherein
a plurality of separation layers having different concentrations of the predetermined undesired substance are formed from the body fluid in the body fluid bag by the centrifugal separator, and
the plurality of separation layers are sent to the filter in order starting with the layer having the highest concentration of the predetermined undesired substance.

10. The chemical liquid addition system according to claim 2, comprising:
a body fluid component bag holding a body fluid component other than the body fluid component that flows to the flow path; and
another flow path that connects the body fluid bag and the body fluid component bag.

11. The chemical liquid addition system according to claim 10, wherein the another flow path is connected to the end of the body fluid bag on the side in the direction of centrifugal force of the centrifugal separator when the system is placed on the centrifugal separator.

12. The chemical liquid addition system according to claim 2, wherein
the body fluid is blood,
the body fluid component flowing to the flow path is a red cell component composed mainly of red blood cells, and
the chemical liquid is a preservation liquid for preserving the red cell component.

13. The chemical liquid addition system according to claim 2, wherein a filter that removes a predetermined undesired substance from the mixed liquid is provided in the flow path.

* * * * *